US009451926B2

(12) United States Patent
Kinahan et al.

(10) Patent No.: US 9,451,926 B2
(45) Date of Patent: Sep. 27, 2016

(54) RESPIRATORY MOTION CORRECTION WITH INTERNAL-EXTERNAL MOTION CORRELATION, AND ASSOCIATED SYSTEMS AND METHODS

(71) Applicants: Paul E. Kinahan, Seattle, WA (US); Adam Alessio, Seattle, WA (US); Chi Liu, Orange, CT (US)

(72) Inventors: Paul E. Kinahan, Seattle, WA (US); Adam Alessio, Seattle, WA (US); Chi Liu, Orange, CT (US)

(73) Assignee: University of Washington through its Center for Commercialization, Seattle, WA (US)

( * ) Notice: Subject to any disclaimer, the term of this patent is extended or adjusted under 35 U.S.C. 154(b) by 62 days.

(21) Appl. No.: 13/891,083

(22) Filed: May 9, 2013

(65) Prior Publication Data

US 2013/0303898 A1    Nov. 14, 2013

Related U.S. Application Data

(60) Provisional application No. 61/644,900, filed on May 9, 2012.

(51) Int. Cl.
| | | |
|---|---|---|
| *A61B 5/05* | (2006.01) | |
| *A61B 6/00* | (2006.01) | |
| *A61B 6/03* | (2006.01) | |

(52) U.S. Cl.
CPC ............ *A61B 6/527* (2013.01); *A61B 6/032* (2013.01); *A61B 6/037* (2013.01); *A61B 6/5235* (2013.01); *A61B 6/5264* (2013.01); *A61B 6/541* (2013.01)

(58) Field of Classification Search
None
See application file for complete search history.

(56) References Cited

U.S. PATENT DOCUMENTS

| | | | | |
|---|---|---|---|---|
| 8,042,209 | B2 * | 10/2011 | D'Souza et al. | 5/610 |
| 8,718,338 | B2 * | 5/2014 | Soubelet et al. | 382/128 |
| 2006/0067458 | A1 * | 3/2006 | Chen | G06T 11/005 378/4 |
| 2006/0074304 | A1 * | 4/2006 | Sayeh | 600/427 |
| 2007/0081704 | A1 * | 4/2007 | Pan et al. | 382/128 |
| 2008/0281192 | A1 * | 11/2008 | Keall et al. | 600/426 |
| 2009/0041188 | A1 * | 2/2009 | Keall et al. | 378/65 |
| 2011/0038452 | A1 * | 2/2011 | Moghe et al. | 378/19 |
| 2012/0004518 | A1 * | 1/2012 | D'Souza et al. | 600/301 |
| 2012/0245453 | A1 * | 9/2012 | Tryggestad et al. | 600/413 |
| 2012/0281897 | A1 * | 11/2012 | Razifar et al. | 382/131 |

FOREIGN PATENT DOCUMENTS

| | | | | |
|---|---|---|---|---|
| WO | WO2006/000789 | * | 1/2006 | A61B 5/113 |

OTHER PUBLICATIONS

Taubin, Gabriel; "Smooth Signed Distance Surface Reconstruction," Brown University (Oct. 20, 2011).*

(Continued)

*Primary Examiner* — Jonathan Cwern
(74) *Attorney, Agent, or Firm* — Perkins Coie LLP

(57) ABSTRACT

The present technology relates generally to respiratory motion correction and associated systems and methods. In particular, several embodiments are directed to respiratory motion correction using internal-external motion correlation. For example, one embodiment of a method of correcting motion blurring in PET/CT imaging includes obtaining PET/CT imaging data of a target tissue in a patient and determining a centroid of the target tissue. The method can further include obtaining an external motion signal of the patient and determining a mean displacement of the external motion signal. The centroid of the target tissue can be correlated with the mean displacement and, based on the correlation, a PET/CT image corrected for motion of the target tissue can be reconstructed.

14 Claims, 4 Drawing Sheets

(56) References Cited

OTHER PUBLICATIONS

"Attenuation-emission alignment in cardiac PET/CT based on consistency conditions", Med. Phys. 37 (3), Mar. 2010.*
A. F. Abdelnour et al., "Phase and Amplitude Binning for 4D-CT Imaging," Phys. Med. Biol. 52, 3515-3529 (2007).
A.L. Kesner et al., "Respiratory gated PET derived in a fully automated manner from raw PET data," IEEE Trans. Nucl. Sci. 56, 677-686 (2009).
A.M. Alessio et al., "Attenuation-emission alignment in cardiac PET/CT based on consistency conditions," Med. Phys. 37, 1191-1200 (2010).
A.M. Alessio et al., "Consistency driven respiratory Phase alignment and motion compensation in PET/CT," IEEE Nuclear Science Symposium and Medical Imaging Conference Record (Honolulu, Hawaii, 2007), vol. 4, pp. 3115-3119.
A.S. Beddar et al., "Correlation between internal fiducial tumor motion and external marker motion for liver tumors imaged with 4D-CT," Int. J. Radiat. Oncol., Biol., Phys. 67, 630-638 (2007).
B. Thorndyke et al., "Reducing Respiratory Motion Artifacts in Positron Emission Tomography Through Retrospective Stacking," Med. Phys. 33, 2632-2641 (2006).
C. Bai et al., "An analytical study of the effects of attenuation on tumor detection in whole-body PET oncology imaging," J. Nucl. Med. 44, 1855-1861 (2003).
C. Liu et al., "Quiescent Period Respiratory Gating for PET/CT," Med. Phys. 37, 5037-5043 (2010).
C. Liu et al., "The Impact of Respiratory Motion on Tumor Quantification and Delineation in Static PET/CT Imaging," Phys. Med. Biol. 54, 7345-7362 (2009).
D. Ionascu et al., "Internal-external correlation investigations of respiratory induced motion of lung tumors," Med. Phys. 34, 3893-3903 (2007).
D. Visvikis et al., "A posteriori respiratory motion gating of dynamic PET images," IEEE Nuclear Science Symposium and Medical Imaging Conference Record (Portland, Oregon, 2003), vol. 5, pp. 3276-3280.
D.P. Gierga et al., "Quantification of respiration-induced abdominal tumor motion and its impact on IMRT dose distributions," Int. J. Radiat. Oncol., Biol., Phys. 58, 1584-1595 (2004).
D.P. Gierga et al., "The correlation between internal and external markers for abdominal tumors: implications for respiratory gating," Int. J. Radiat. Oncol., Biol., Phys. 61, 1551-1558 (2005).
E. Reitzel et al., "Four-Dimensional Computed Tomography: Image Formation and Clinical Protocol," Med. Phys. 32, 874-889 (2005).
F. Buther et al., "List mode-driven cardiac and respiratory gating in PET," J. Nucl. Med. 50, 674-681 (2009).
F. Lamare et al., "List-mode-based reconstruction for respiratory motion correction in PET using non-rigid body transformations," Phys. Med. Biol. 52, 5187-5204 (2007).
F. Qiao et al., "A Motion-Incorporated Reconstruction Method for Gated PET Studies," Phys. Med. Biol. 51, 3769-3783 (2006).
F. Qiao et al., "Joint model of motion and anatomy for PET image reconstruction," Med. Phys. 34, 4626-4639 (2007).
F. Qiao et al., "Region of interest motion compensation for PET image reconstruction," Phys. Med. Biol. 52, 2675-2689 (2007).
G.J. Klein et al., "Fine-scale motion detection using intrinsic list mode PET information," IEEE Workship on Mathematical Methods in Biomedical Image Analysis (Kauai, Hawaii, 2001), pp. 71-78.
G.S. Meirelles et al., "Deep-inspiration breath-hold PET/CT: clinical findings with a new technique for detection and characterization of thoracic lesions," J. Nucl. Med. 48, 712-719 (2007).
H.M. Hudson et al., "Accelerated image reconstruction using ordered subsets of projection data," IEEE Trans. Med. Imaging 13, 601-609 (1994).
J.D. Hoisak et al., "Correlation of lung tumor motion with external surrogate indicators of respiration," Int. J. Radiat. Oncol., Biol., Phys. 60, 1298-1306 (2004).
J.W. Wolthaus et al., "Fusion of Respiration-Correlated PET and CT Scans: Correlated Lung Tumour Motion in Anatomical and Functional Scans," Phys. Med. Biol. 50, 1569-1583 (2005).
M. Dawood et al., "Lung motion correction on respiratory gated 3-D PET/CT images," IEEE Trans. Med. Imaging 25, 476-485 (2006).
M. Dawood et al., "Respiratory Gating in Positron Emission Tomography: A Quantitative Comparison of Different Gating Schemes," Med. Phys. 34, 3067-3076 (2007).
M. Guckenberger et al., "Influence of Retrospective Sorting on Image Quality in Respiratory Correlated Computed Tomography," Radiother. Oncol. 85, 223-231 (2007).
N. Wink et al., "Phase Versus Amplitude Sorting of 4D-CT Data," J. Appl. Clin. Med. Phys. 7, 77-85 (2006).
P.E. Kinahan et al., "Compensating for patient respiration in PET/CT imaging with the registered and summed phases (RASP) procedure," IEEE International Symposium on Biomedical Imaging (Arlington, Virginia, 2006), vol. 2, p. 1104.
P.E. Kinahan et al., "Impact of respiration variability on respiratory gated whole-body PET/CT imaging," J. Nucl. Med. 48, 196 (2007).
P.E. Kinahan et al., "X-ray-based attenuation correction for positron emission tomography/computed tomography scanners," Semin. Nucl. Med. 33, 166-179 (2003).
P.J. Schleyer et al., "Retrospective data-driven respiratory gating for PET/CT," Phys. Med. Biol. 54, 1935-1950 (2009).
R. Manjeshwar et al., "Motion Compensated Image Reconstruction for Four-Dimensional PET/CT," 3rd IEEE International Symposium on Biomedical Imaging (Arlington, Virginia, 2006), pp. 674-677.
R.A. Bundschuh et al., "Postacquisition detection of tumor motion in the lung and upper abdomen using list-mode PET data: a feasibility study," J. Nucl. Med. 48, 758-763 (2007).
S. A. Nehmeh et al., "Four-Dimensional (4D) PET/CT Imaging of the Thorax," Med. Phys. 31, 3179-3186 (2004).
S. Senan et al., "Literature-based recommendations for treatment planning and execution in high-dose radiotherapy for lung cancer," Radiother. Oncol. 71, 139-146 (2004).
S.A. Nehmeh and Y.E. Erdi, "Respiratory Motion in Positron Emission Tomography/Computed Tomography: A Review," Semin. Nucl. Med. 38, 167-176 (2008).
S.A. Nehmeh et al., "Deep-inspiration breath-hold PET/CT of the thorax," J. Nucl. Med. 48, 22-26 (2007).
S.A. Nehmen et al., "Quantitation of respiratory motion during 4D-PET/CT acquisition," Med. Phys. 31, 1333-1338 (2004).
T. Kawano, E. Ohtake, and T. Inoue, "Deep-Inspiration Breath-Hold PET/CT of Lung Cancer: Maximum Standardized Uptake Value Analysis of 108 Patients," J. Nucl. Med. 49, 1223-1231 (2008).
T. Li et al., "Model-Based Image Reconstruction for Four-Dimensional PET," Med. Phys. 33, 1288-1298 (2006).
T. Pan et al., "4D-CT Imaging of a Volume Influenced by Repiratory Motion During 4D-PET/CT Acquisition," Med. Phys. 31, 1333-1338 (2004).
T. Pan et al., "Improvement of the Cine-CT Based 4D-CT Imaging," Med. Phys. 34, 4499-4503 (2007).
T. Torizuka et al., "Single 20-second acquisition of deep-inspiration breath-hold PET/CT: Clinical feasibility for lung cancer," J. Nucl. Med. 50, 1579-1584 (2009).
T. Yamazaki et al., "An attenuation correction method for respiratory-gated PET/CT image," IEEE Nuclear Science Symposium and Medical Imaging Conference Record (San Diego, California, 2006), pp. 3292-3296.
T.B. Sebastian et al., "Objective PET lesion segmentation using a spherical mean shift algorithm," Med. Image Comput. Comput. Assist Interv. 2006, vol. 9, pp. 782-789.
W. A. Weber, "Assessing Tumor Response to Therapy," J. Nucl. Med. 50 (Suppl. 1) 1S-10S (2009).
W. Lu et al., "A Comparison Between Amplitude Sorting and Phase-Angle Sorting Using External Respiratory Measurement for 4D CT," Med. Phys. 33, 2964-2974 (2006).
Y. Seppenwoolde et al;, "Precise and real-time measurement of 3D tumor motion in lung due to breathing and heartbeat, measured during radiotherapy," Int. J. Radat. Oncol., Biol., Phys. 53, 822-834 (2002).
Y.E. Erdi et al., "The CT Motion Quantitation of Lung Lesions and its impact on PET-measures SUVs" J. Nucl. Med. 45, 1287-1292 (2004).

* cited by examiner

RESPIRATORY MOTION CORRECTION WITH INTERNAL-EXTERNAL MOTION CORRELATION, AND ASSOCIATED SYSTEMS AND METHODS

CROSS-REFERENCE TO RELATED APPLICATION

The present application claims the benefit of U.S. Provisional Patent Application No. 61/644,900, filed May 9, 2012. The foregoing application is incorporated herein by reference in its entirety. Further, components and features of embodiments disclosed in the application incorporated by reference may be combined with various components and features disclosed and claimed in the present application.

STATEMENT REGARDING FEDERALLY-SPONSORED RESEARCH

This invention was made with government support under R01-CA115870 awarded by the National Institutes of Health. The government has certain rights in the invention.

TECHNICAL FIELD

The present technology relates generally to respiratory motion correction and associated systems and methods. In particular, several embodiments are directed to respiratory motion correction using internal-external motion correlation.

BACKGROUND

Positron Emission Tomography-Computed Tomography ("PET/CT") is a medical imaging technique that combines Positron Emission Tomography ("PET") and x-ray Computed Tomography ("CT"). Images acquired from both types of systems can be taken in the same session and combined into a single superposed (co-registered) image. Functional imaging obtained by PET scanning, which depicts the spatial distribution of metabolic or biochemical activity in the body, can be aligned or correlated with anatomic imaging obtained by CT scanning PET/CT has become an important tool to assess the response to therapy for cancer patients. However, respiratory motion can have a major degrading impact on PET-based tumor quantification and delineation. For example, respiratory motion can lead to a tracer concentration underestimation of 30% or more, and overestimation of tumor volume by a factor of two or more. To correct for respiratory motion, the most widely used method is respiratory-gated PET/CT, which divides PET data into different gates based on either temporal phase or respiratory displacement information with potential four-dimensional CT for phase-matched attenuation correction. However, since each gated image contains only a fraction of the detected coincidence events, the increased image noise can lead to substantial overestimation of tracer concentration measured by maximum standardized uptake value (SUVmax).

Another category of motion correction methods utilizes all the detected coincident events, leading to no increase in image noise compared to the static ungated PET image. These methods typically start with respiratory-gated PET or CT data and incorporate estimated image-based motion vectors either into the image reconstruction or postprocessing. The image-based motion vector used in these methods can be derived either from respiratory-gated PET or CT images. If estimated from gated PET images, the motion vectors are subject to the high levels of image noise, and the estimation errors can propagate into the motion-corrected images. On the other hand, gated CT images have much lower noise and can potentially generate more accurate motion vectors, but the patient motion during CT acquisition can be very different from the motion during PET acquisition because of respiration variations. In addition, these approaches may require nonrigid volumetric image registration, which is sensitive to numerous free parameters and typically does not preserve PET tracer concentration. Further, these approaches do not correct for intra-gate motion due to inter-cycle and intra-cycle breathing variation. Alternatives to gating are breath-hold PET/CT methods, which require patients to hold their breath repeatedly during the PET and/or CT acquisition. The breath-hold PET/CT images have the potential for less respiratory motion-blurring effects and more accurately aligned PET/CT images. However, this method is difficult to universally apply, as many patients (e.g., patients with lung cancer) are unable to tolerate holding their breath during treatment.

DETAILED DESCRIPTION

The present technology relates generally to respiratory motion correction and associated systems and methods. In particular, several embodiments are directed to respiratory motion correction using internal-external motion correlation. For example, one embodiment of a method for correcting motion blurring in PET/CT imaging includes obtaining PET/CT imaging data of a target tissue in a patient and determining a centroid of the target tissue. The method can further include obtaining an external motion signal of the patient and determining a mean displacement of the external motion signal. The centroid of the target tissue can be correlated with the mean displacement and, based on the correlation, a PET/CT image corrected for motion of the target tissue can be reconstructed.

Specific details of several embodiments of the technology are described below with reference to FIGS. 1-4. Other details describing well-known structures and systems often associated with motion correction and anatomical scanning devices have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1-4.

Figure 1:
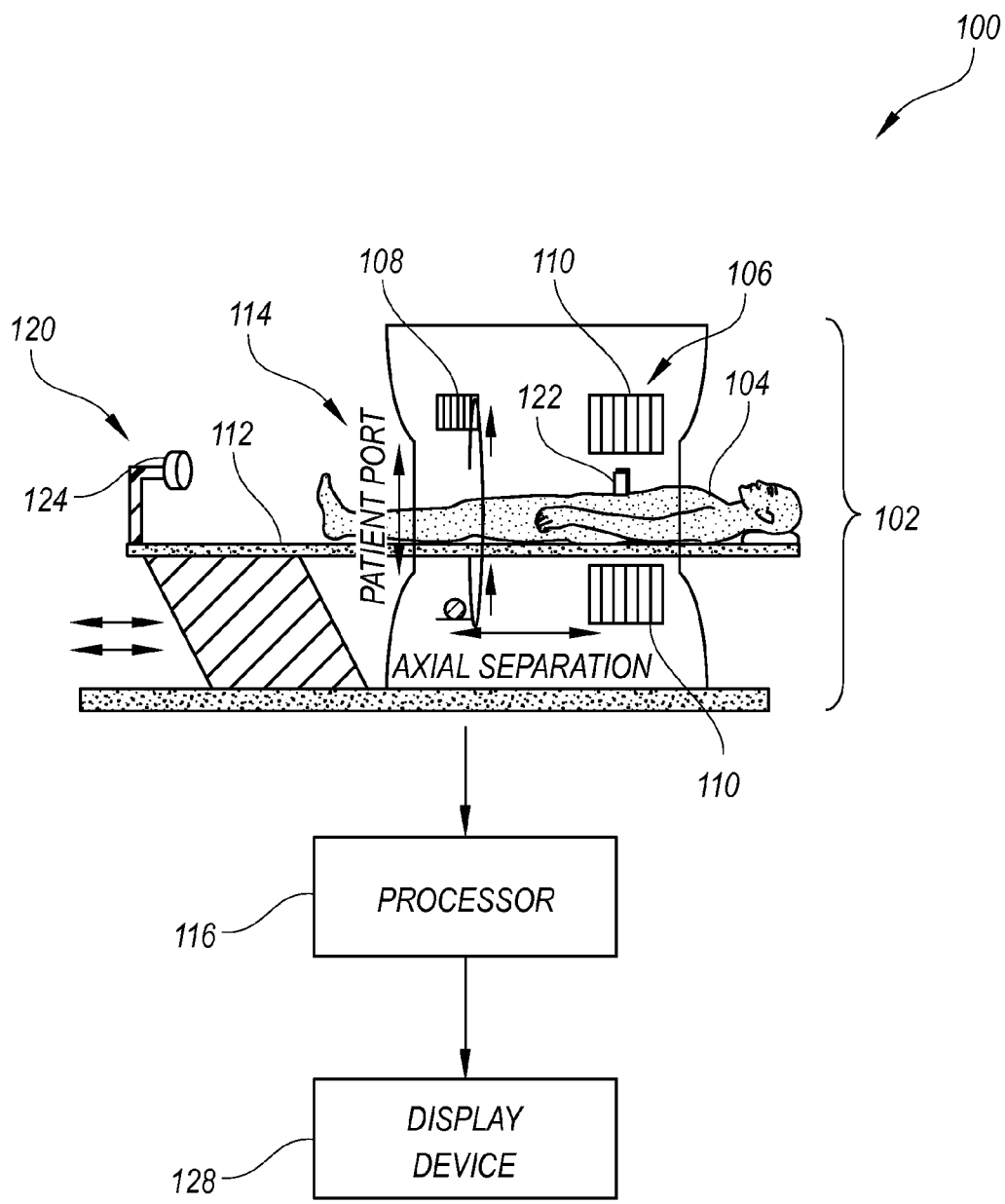
FIG. 1 is a schematic illustration of a respiratory motion correction system configured in accordance with embodiments of the technology.

FIG. 1 is a schematic illustration of a respiratory motion correction system 100 configured in accordance with embodiments of the technology. The motion correction system 100 includes an imaging system 102 positioned proximate to a patient 104. In some embodiments, the imaging system 102 includes a PET imaging component 106 and a CT imaging component 108. For example, in the illustrated embodiment, the PET imaging component 106 includes one or more stationary PET detectors 110 at least partially surrounding the patient 104 positioned on a bed 112. In some embodiments, the CT imaging component 108, such as a helical CT scanner, can be axially separated from the stationary PET detectors 110 such that the patient 104 positioned on the bed 112 enters a patient port 114 of the imaging system 102 and successively interfaces with the CT imaging component 108 and the PET imaging component 106. In further embodiments, the imaging system 102 comprises additional or alternate types of imaging components, or the PET imaging component 106 and CT imaging component 108 can take on any other arrangement known in the art. As with traditional PET/CT systems, the imaging system 102 can obtain and record functional imaging data having anatomic localization. For example, the imaging system 102 can be used to obtain data related to the size, volume, and/or tracer uptake in a target tissue, such as a tumor. In particular embodiments, the target tissue may be located in the chest, abdomen, lower abdomen, thorax, pancreas, kidney, or cardiac system. In further embodiments, the target tissue can be any tissue suitable for scanning using a dynamic imaging system.

The motion correction system 100 further includes an external motion monitor 120. In some embodiments, the motion monitor 120 can include a motion marker 122 and a marker deviation detector 124. In particular embodiments, the motion marker 122 comprises a reflective block positioned on a chest or abdominal region of the patient 104 and the marker deviation detector 124 comprises the Real-time Position Management™ ("RPM") manufactured by Varian Medical Systems. In other embodiments, the marker deviation detector 124 comprises the Anzai Respiratory Gating System manufactured by Anzai Medical. In still further embodiments, however, the motion marker 122 and/or the marker deviation detector 124 may comprise other suitable devices. The motion correction system 100 can be used to measure the patient's respiratory pattern and/or range of motion and record and/or transmit this data as an external motion signal, such as a waveform. In further embodiments, the external motion monitor 120 need not include both the motion marker 122 and the marker deviation detector 124, but can comprise any system capable of receiving, recording, and/or transmitting data regarding patient movement. In further embodiments, the external motion monitor 120 includes one or more of the following: a stretching belt, a still or video camera capturing the patient's movement (e.g., chest movement), a temperature sensor (e.g., positioned proximate to the patients nose or mouth), other sensor, or another suitable motion or respiratory monitor.

The motion correction system 100 can further include a processor 116 configured to receive and process data from the imaging system 102 and the external motion monitor 120 and reconstruct a PET/CT image corrected for motion of the target tissue. More specifically, in a particular embodiment, based on the external motion signal acquired by the external motion monitor 120, imaging data (e.g., PET listmode data) can be binned into a number of phase frames with equal counts and each frame can be reconstructed. In some embodiments, for example, the frames can be reconstructed using an ordered subset expectation maximization algorithm with two iterations and 28 subsets and smoothed with an 8 mm Gaussian postreconstruction filter. In particular embodiments, the PET listmode data can be binned into five or eight phase frames. In other embodiments, however, the imaging data can be binned into other numbers of phase frames and/or other algorithms or filters can be employed. For example, in some embodiments, another image reconstruction algorithm, such as an iterative image reconstruction algorithm, can be used.

In some embodiments, the processor 116 can segment the target tissue in each reconstructed phase frame and determine the centroids of the segmented tissue. The processor 116 can further determine and record data corresponding to respiratory displacements that correspond to each phase frame, such as the mean and/or median displacements of the external motion signal. The target tissue centroid locations in the phase-gated images can be correlated with the mean displacements of corresponding external motion signals. In some embodiments, for example, the relationship between the target tissue centroids and external motion signal mean displacements may be estimated with a linear function. This linear function can be used to convert the original external motion signal into an internal tumor motion signal with high temporal resolution. As will be described in further detail below with reference to FIGS. 2A and 2B, each image frame can be registered to a reference location and the aligned frames can be summed to generate a motion-corrected image. Corrections for attenuation, scatter, random coincidences, dead time, and detector efficiency can be included in the reconstruction. In further embodiments, other reconstruction methods, algorithms, iterations, or filters can be used. In some embodiments, the reconstructed image can be passed to a display device 128 for user review.

While the processor 116 has been illustrated as a single component for purposes of clarity, in several embodiments one or more processors can be used to execute instructions to perform various combinations of the tasks described above. For example, in some embodiments, separate processors can perform the tasks ascribed to the single processor 116 described above, and in various embodiments these tasks can be processed sequentially or concurrently. Further, while the motion correction system 100 has been discussed in terms of correcting imaging for a single target tissue, in various embodiments, the motion correction system 100 can be used to correct for motion of a plurality of tumors, either successively or concurrently. Additionally, in various embodiments, image correction can be performed in the superior-inferior, anterior-posterior and/or left-right directions.

Figure 2A:
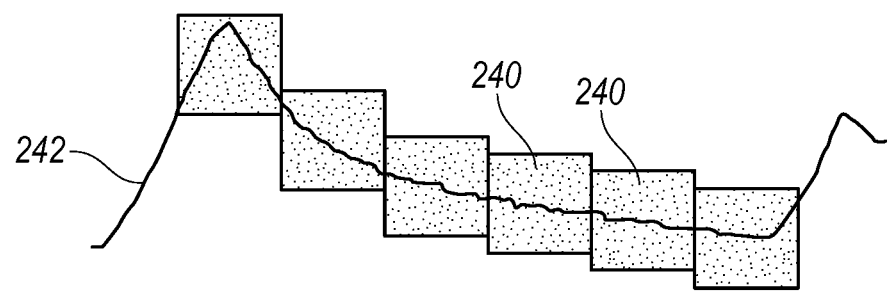
FIG. 2A is a schematic illustration of a portion of pre-corrected sinograms in accordance with embodiments of the technology.
Figure 2B:
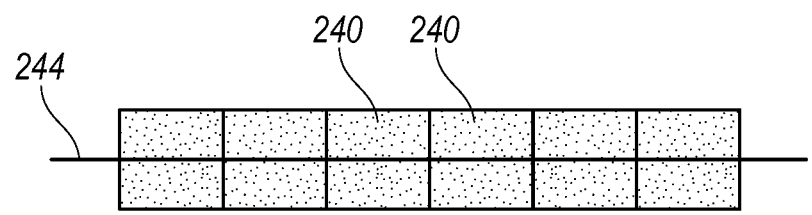
FIG. 2B is a partially schematic illustration of a portion of the sinograms of FIG. 2A after postcorrection based on internal tumor motion information in accordance with embodiments of the technology.

FIG. 2A is a partially schematic illustration of a portion of precorrected sinograms 240 in accordance with embodiments of the technology. In some embodiments, the listmode data from the imaging system 102 described above with reference to FIG. 1 can be binned into sequential 1-second (1-s) dynamic frames. Each box represents a 1-s sinogram 240 and its vertical position corresponds to the target tissue location before correction. In further embodiments, each box can represent a sinogram 240 with an interval other than 1-s or each detected listmode data event. The sinograms 240 are superimposed on an internal tumor motion trace 242 captured by the imaging system 102. In another embodiment, the listmode data itself, with arbitrarily fine time sampling, can be corrected for motion before binning FIG. 2B is a partially schematic illustration of a portion of the sinograms 240 of FIG. 2A after postcorrection based on internal tumor motion information in accordance with embodiments of the technology. The vertical position of each sinogram 240 corresponds to the target tissue location after correction. According to the internal location data and external motion signal of a given target tissue, each 1-s dynamic frame can be axially registered to a reference location 244 using linear interpolation. All the aligned frames can be summed to generate a motion-corrected sinogram, which can be subsequently reconstructed using the ordered subset expectation maximization algorithm described above, with corrections for attenuation, scatter, and random coincidence to form a motion-corrected image (e.g., a PET image).

In some embodiments, the choice of reference location 244 can be determined with a consideration for axially-aligned attenuation correction. For example, the helical CT images for attenuation correction may be mismatched with the PET images due to patient respiratory motion. To minimize the attenuation correction mismatch, the reference frame (at the reference location 244), to which other 1-s dynamic frames are shifted, can be selected based on the two-dimensional Radon consistency conditions of the attenuation correction data. These conditions state the moments of the projections through the activity object and can be periodic with azimuthal angle. For example, the zero-order moment describes the property that the sum of the projection data for each view of a set of parallel-beam projections is a constant, independent of the projection angle. In a particular embodiment, the attenuation correction from the single helical CT can be applied to each of the five phase gated PET frames. The attenuation-corrected PET frame that best matches the first three moments of the two-dimensional Radon consistency conditions can be considered to have the best positional match with the attenuation map. This approach evaluates the Radon consistency conditions in a global manner for the whole PET bed position image. Therefore, small local nonrigid distortions caused by respiratory motion and/or CT mismatch are not expected to have a negative impact on the image quality. The mean displacement of this best-matched PET frame can be used as the reference location 244 for the subsequent axial shifts of all the 1-s frames.

In further embodiments, implementing image correction can be performed in the superior-inferior, left-right and/or anterior-posterior directions. For example, the techniques described herein can be used to achieve fully three-dimensional correction for respiratory motion. In some embodiments, three-dimensional correction can be performed in image space by individually reconstructing each 1-s frame first, then registering, and then averaging. In further embodiments, the motion in listmode or sinogram space can first be corrected. For example, the external motion signal can be converted into three separate internal tumor motion signals in the superior-inferior, left-right, and anterior-posterior directions, respectively. The motion vectors determined by internal motion traces in the image space can be forward-projected onto the sinogram space to establish necessary motion information to guide the sinogram registration or listmode repositioning. The fully three-dimensional motion-corrected sinograms could then be summed and reconstructed as described above.

Figure 3:
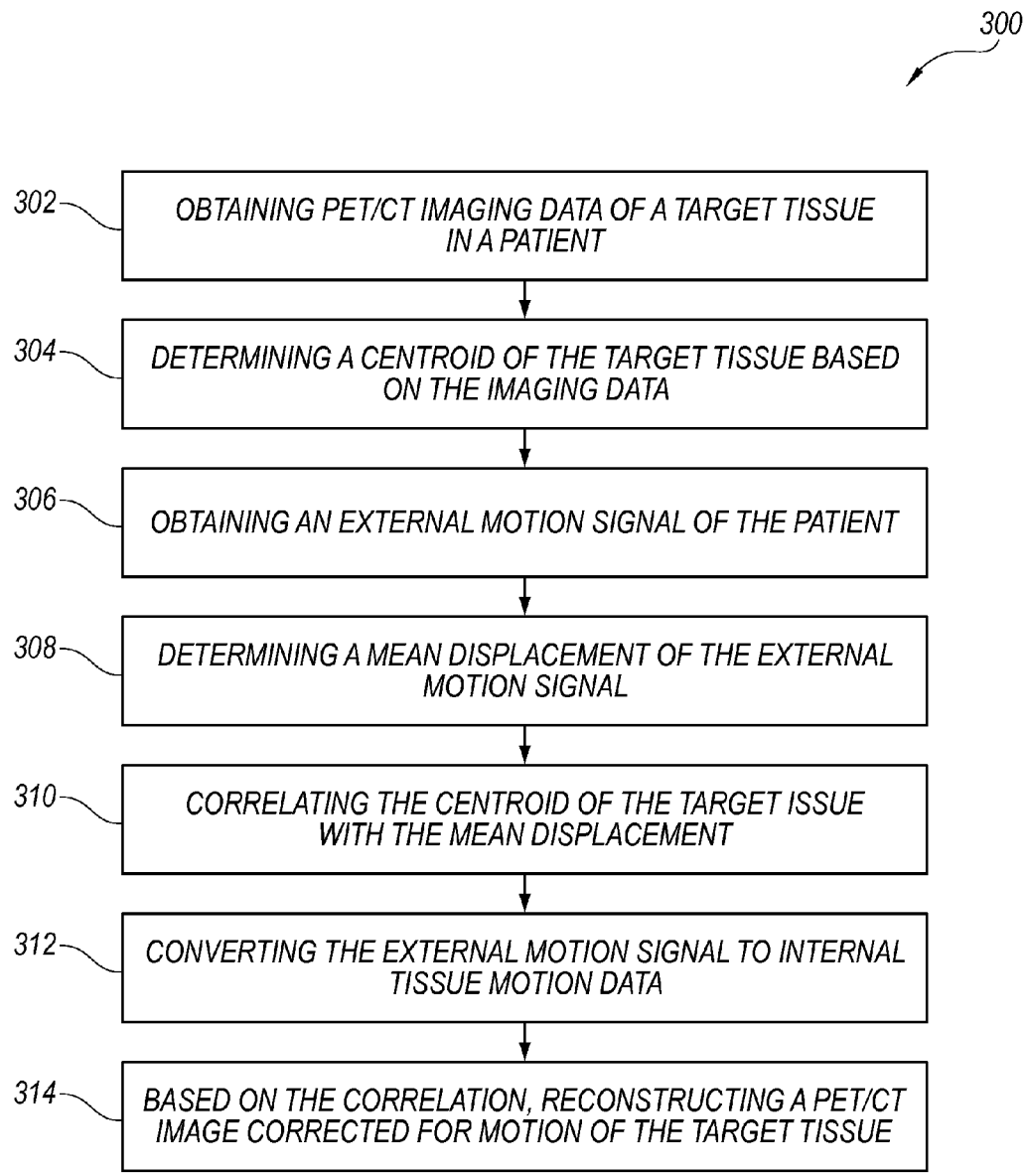
FIG. 3 is a block diagram illustrating a method of correcting motion blurring in PET/CT imaging in accordance with embodiments of the technology.

FIG. 3 is a block diagram illustrating a method 300 of correcting motion blurring in PET/CT imaging in accordance with embodiments of the technology. The method 300 at block 302 includes obtaining PET/CT imaging data of a target tissue in a patient. In some embodiments, for example, the imaging data comprises a target tumor in a lung or abdomen region of the patient. At block 304, the method 300 includes determining a centroid of the target tissue based on the imaging data.

The method 300 continues at blocks 306 and 308 with obtaining an external motion signal of the patient and determining a mean displacement of the external motion signal. In some embodiments, the external motion signal is obtained using one or more of a marker on a chest or abdomen region of the patient and monitoring motion of the marker. At block 310, the method 300 includes correlating the centroid of the target tissue with the mean displacement. In some embodiments, for example, this correlation is done by estimating the relationship between the centroid of the target and the mean displacement using a fitted function which can be linear or non-linear.

At block 312, the method 300 includes converting the external motion signal into internal tissue motion data according to the correlation established above. In some embodiments, the method 300 further includes binning at least a portion of the imaging data into a plurality of phase frames. Each individual phase frame can be reconstructed using, for example, an ordered subset expectation maximization algorithm. In further embodiments, each individual phase frame can be reconstructed by registering each phase frame to a reference location using linear interpolation.

At block 314, the method 300 includes reconstructing a PET/CT image corrected for motion of the target tissue based on the correlation. In various embodiments, the PET/CT image can be corrected for at least one of superior-inferior, left-right, or anterior-posterior motion of the target tissue. In some embodiments, reconstructing the PET/CT image comprises removing respiratory motion of the target tissue without increasing a quantity of noise in the image. In some embodiments, the image is corrected for attenuation, scatter, random coincidences, dead time, and/or detector efficiency.

Figure 4:
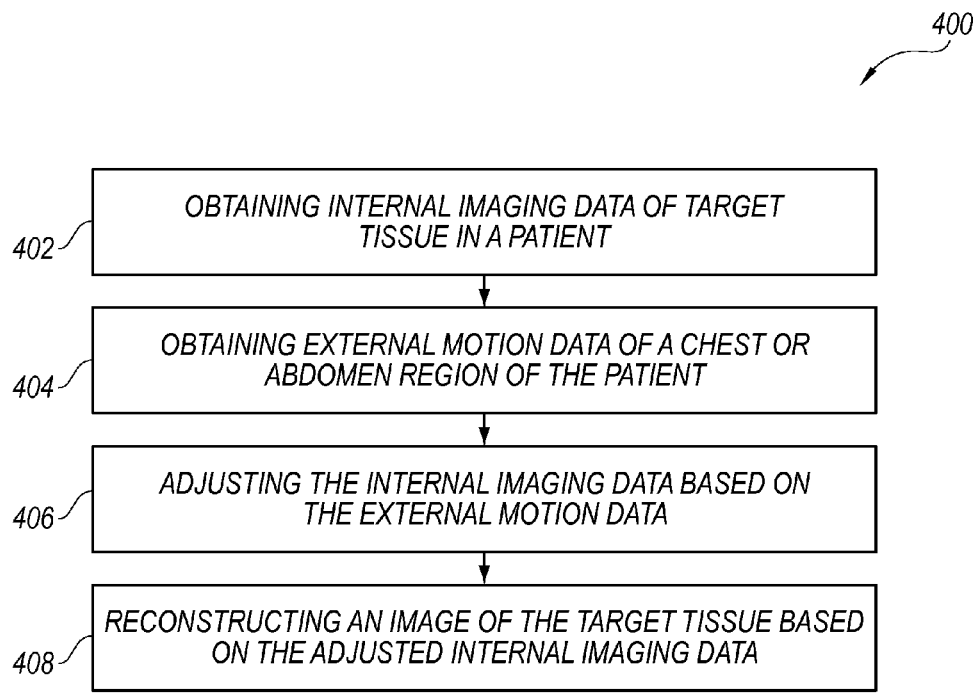
FIG. 4 is a block diagram illustrating a method of quantifying a target tissue in accordance with embodiments of the technology.

FIG. 4 is a block diagram illustrating a method 400 of quantifying a target tissue in accordance with embodiments of the technology. At block 402, the method 400 includes obtaining internal imaging data of a target tissue in a patient, such as PET/CT imaging data. At block 404, the method 400 includes obtaining external motion data of a chest or abdomen region of the patient. In some embodiments, the method 400 includes determining (a) a centroid of the target tissue based on the internal imaging data and (b) a mean displacement of the external motion data.

At block 406, the method 400 further includes adjusting the internal imaging data based on the external motion data. For example, the internal imaging data can be adjusted by correlating the centroid of the target tissue with the mean displacement. The method 400 also includes, at block 408, reconstructing an image of the target tissue based on the adjusted internal imaging data. In some embodiments, the method 400 further includes quantifying a target tissue volume or a tracer concentration in the target tissue.

The present technology offers several advantages over traditional motion correction systems. For example, the motion correction technology described herein can improve quantification and delineation of known tumors for assessing response to therapy and treatment planning Compared to conventional motion correction methods, such as respiratory-gating methods that include only a fraction of the detected events and yield higher image noise, the technology described herein can correct for respiratory motion without increasing image noise. Furthermore, the motion correction can be applied at a finer temporal resolution than corrections applied to conventional respiratory-gated images. These advantages are particularly important for tumor quantification, as increased image noise alone can cause significant tracer uptake overestimation. While conventional motion correction methods typically cannot correct for intra-gate motion, the technology described herein can correct for intra-gate motion to improve quantification.

Further, mismatched attenuation correction can cause tumor quantification errors, particularly with CT-based attenuation correction that can be acquired at an arbitrary breathing displacement when the patient is under free breathing during the acquisition. Using the present technology, for example, each 1-s sinogram can be registered to a reference frame that is best aligned with the helical CT image as determined by the Radon consistency conditions. Therefore, after summing all the registered sinograms, the summed sinogram can be reconstructed with attenuation correction using a matched attenuation map. This is expected to minimize attenuation correction errors.

From the foregoing it will be appreciated that, although specific embodiments of the technology have been described herein for purposes of illustration, various modifications may be made without deviating from the spirit and scope of the technology. While some embodiments have been discussed in terms of quantifying tumors in the lung and abdomen region, in further embodiments, the image processing can be performed for target tissue in the lower abdomen, thorax, pancreas, kidney, cardiac system, or other systems suitable for use with dynamic imaging. Further, certain aspects of the new technology described in the context of particular embodiments may be combined or eliminated in other embodiments. Moreover, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A method of correcting motion blurring in positron emission tomography-computed tomography ("PET/CT") imaging, the method comprising:
   obtaining PET/CT imaging data of a target tissue in a patient via an imaging system positioned proximate to the patient;
   determining a centroid of the target tissue;
   obtaining an external motion signal of the patient;
   determining a mean displacement of the external motion signal;
   correlating the centroid of the target tissue with the mean displacement;
   selecting a reference frame from a plurality of PET reference frames, wherein the selected reference frame is based, at least in part, on one PET reference frame from the plurality of PET frames that best matches Radon consistency conditions and attenuation correction data; and
   based on the correlation and the selected reference frame, reconstructing a PET/CT image corrected for motion of the target tissue.

2. The method of claim 1, further comprising binning at least a portion of the PET/CT imaging data into a plurality of phase frames.

3. The method of claim 2 wherein reconstructing the PET/CT image comprises reconstructing each of the individual phase frames.

4. The method of claim 3 wherein reconstructing each of the individual phase frames comprises reconstructing the phase frames using an ordered subset expectation maximization algorithm or iterative image reconstruction algorithm.

5. The method of claim 3 wherein reconstructing each of the individual phase frames comprises registering each individual phase frame to a reference location using linear interpolation.

6. The method of claim 1 wherein correlating the centroid of the target tissue with the mean displacement comprises estimating a relationship between the centroid of the target tissue and the mean displacement using a fitted function.

7. The method of claim 1 wherein obtaining an external motion signal of the patient comprises positioning a marker on a chest or abdomen region of the patient and monitoring motion of the marker.

8. The method of claim 1 wherein reconstructing the PET/CT image corrected for motion of the target tissue comprises reconstructing the PET/CT image corrected for at least one of superior-inferior, left-right, or anterior-posterior motion of the target tissue.

9. The method of claim 1 wherein obtaining PET/CT imaging data of the target tissue comprises obtaining the PET/CT imaging data of a target tissue in the patient's chest, abdomen, lower abdomen, thorax, pancreas, kidney, or cardiac system.

10. The method of claim 1 wherein reconstructing the PET/CT image corrected for motion of the target tissue comprises removing respiratory motion of the target tissue without increasing a quantity of noise in the PET/CT image.

11. The method of claim 1, further comprising correcting the PET/CT image for attenuation, scatter, random coincidences, dead time, and detector efficiency.

12. A motion correction system for imaging a target tissue of a patient using positron emission tomography-computed tomography ("PET/CT"), the system comprising:
   a PET/CT imaging system configured to be positioned proximate to the patient and record location data corresponding to a centroid of the target tissue;
   an external motion marker configured to generate an external motion signal; and
   a physical computer-readable storage medium having stored thereon, computer-executable instructions that, if executed by a computing system, cause the computing system to perform operations comprising:
      receiving the location data and the external motion signal;
      correlating a mean displacement of the external motion signal with the location data;
      converting the external motion signal to tissue location data;
      selecting a reference frame from a plurality of PET reference frames ,wherein the selected reference frame is based, at least in part, on one PET reference frame from the plurality of PET frames that best matches Radon consistency conditions and attenuation correction data; and based on the correlation and the selected reference frame, reconstructing a PET/CT image corrected for motion of the target tissue.

13. A system of claim 12 wherein the external motion marker comprises one or more of a reflective block, a stretching belt, a still or video camera, or a temperature sensor.

14. The system of claim 12 wherein the computer-executable instructions further cause the computing system to perform operations comprising:
   binning at least a portion of the location data into a plurality of phase frames;
   reconstructing each of the individual phase frames; and
   registering each of the individual phase frames to a reference location and summing the phase frames to generate a final PET/CT image.

* * * * *